United States Patent [19]
Ajot et al.

[11] Patent Number: 5,569,839
[45] Date of Patent: Oct. 29, 1996

[54] METHOD AND APPARATUS FOR DETERMINING PORE VOLUME IN A SOLID SAMPLE

[75] Inventors: Hubert Ajot, deceased, late of Rueil Malmaison, by Christine Ajot, legal representative; by Laure Ajot, legal representative, Argenteuil; by Alexandra Ajot, legal representative, Rueil Malmaison; by Vincent Ajot, legal representative, Le Vesinet; Colette Russmann, Eaubonne; Jose Brandely, Savigny Sur Orge; Dominique Garnier, Orgeval; Pierre Gonzalez, Rueil Malmaison, all of France

[73] Assignee: Institut Francais Du Petrole, Rueil Malmaison, France

[21] Appl. No.: 342,034

[22] Filed: Nov. 17, 1994

[30] Foreign Application Priority Data

Nov. 17, 1993 [FR] France ................. 93 13817

[51] Int. Cl.⁶ ............................................. G01N 15/08
[52] U.S. Cl. ............................................. 73/38
[58] Field of Search ....................................... 73/38

[56] References Cited

U.S. PATENT DOCUMENTS

| | | |
|---|---|---|
| 3,158,020 | 11/1964 | Donaldson ................. 73/38 |
| 4,170,129 | 10/1979 | Lowell ....................... 73/38 |
| 4,513,603 | 4/1985 | Baillie ......................... 73/38 |
| 4,524,605 | 6/1985 | Italiano et al. ............... 73/38 |
| 4,625,544 | 12/1986 | Hi-Hwa Yuan et al. ..... 73/38 |
| 5,299,140 | 3/1994 | Ankeny et al. .............. 73/38 |

FOREIGN PATENT DOCUMENTS

| | | | |
|---|---|---|---|
| 0201118 | 12/1986 | European Pat. Off. . | |
| 3602511 | 7/1987 | Germany ................... | 73/38 |
| 218638 | 12/1983 | Japan ........................ | 73/38 |
| 39540 | 2/1989 | Japan ........................ | 73/38 |
| 2016709 | 9/1979 | United Kingdom . | |

*Primary Examiner*—Hezron E. Williams
*Assistant Examiner*—Daniel S. Larkin
*Attorney, Agent, or Firm*—Millen, White, Zelano, & Branigan, P.C.

[57] ABSTRACT

The invention concerns an apparatus and method for determining pore volume parameters of a solid sample. The apparatus comprises a high pressure cell (50), a sample holder (1) provided with an orifice (21), means (2) for creating a vacuum connected to a chamber (10a) containing the sample holder by at least one orifice (30), and a mercury supply. The apparatus also comprises a syringe pump (9) connected to the chamber and to mercury supply means for delivery of mercury under pressure, means for programming a steady supply of mercury for a fixed period of time connected to the pump, at least one pressure sensor (15) downstream of the pump which continuously reads the pressure, and means (41) for signal collection and processing connected to the pressure sensor and the means for programming a steady supply of mercury and adapted to calculate the porosimetry parameters.

11 Claims, 3 Drawing Sheets

METHOD AND APPARATUS FOR DETERMINING PORE VOLUME IN A SOLID SAMPLE

FIELD OF THE INVENTION

The invention concerns an apparatus and method for determining pore volume parameters of a solid sample. The apparatus comprises a high pressure cell (50), a sample holder (1) provided with an orifice (21), means (2) for creating a vacuum connected to a chamber (10a) containing the sample holder by at least one orifice (30), and a mercury supply. The apparatus also comprises a syringe pump (9) connected to the chamber and to mercury supply means for delivery of mercury under pressure, means for programming a steady supply of mercury for a fixed period of time connected to the pump, at least one pressure sensor (15) downstream of the pump which continuously reads the pressure, and means (41) for signal collection and processing connected to the pressure sensor and the means for programming a steady supply of mercury and adapted to calculate the porosimetry parameters.

The present invention concerns a method and apparatus for the continuous measurement of mercury intrusion into a porous solid. It can also be applied to the extrusion of mercury from the solid. It further concerns the use of this apparatus in a method for determining the pore volume of a material.

The characterisation of solids by determining the pore volume is of importance in a number of major industrial areas such as catalysis and adsorption, the study of reservoir rocks, minerals, coal, the cement and concrete industry, ceramics, polymers and in general the study of any body which exhibits macroporosity, mesoporosity and/or any microporosity.

Pore volume and pore distribution in a solid obeys Kelvin's law for a non wetting liquid. When a non wetting liquid, for example mercury, penetrates into a capillary of radius r, the force opposing penetration is:

$$F = 2\pi r Y \cos\theta$$

Y=surface tension
θ=contact angle of liquid with solid wall
If penetration is forced by applying pressure P to the liquid, the capillary or pore will fill when $$\pi r^2 P = 2\pi r Y \cos\theta, \text{ ie.,}$$

$$P = -\frac{2Y\cos\theta}{r}$$

Y=485 dynes cm$^{-1}$ at 20° C.
θ varies between 110° and 160° depending on the material.

Application of this formula constitutes the basis of determination. Any pressure greater than the fixed value for pores with radius r causes penetration of mercury into pores with radius r.

Commercial porosimeters can reach pressures of the order of $5.10^2$ MPa, corresponding to pore diameters of 30 Å.

The prior art is illustrated in European patent application EP-A-0 201 118 and United Kingdom application GB-A-2 016 709.

The most widely used apparatus (U.S. Pat. Nos. 3,882, 714, 3,371,519, 3,371,520 and 4,524,605) comprise sample holders provided with a mercury-filled capillary tube immersed in a bath of compression fluid. The compression fluid applies an increasing pressure to the capillary column by means of a pump. A capacitance detector follows the variation in the level of mercury in the column as a function of the pressure. The capillary must be partially or completely coated with a sheath which is expensive and fragile, INCONEL for example, which can fairly easily change and alter the readings. In addition, pressurising the mercury by means of an intermediate fluid introduces other sources of inherent errors, in particular due to the non negligible compressibility of the fluid. Finally, the pressure is increased in stages, meaning that thermodynamic equilibrium is not always observed, thus adversely affecting the quality of the evaluation.

One of the objects of the invention is to overcome these problems.

SUMMARY OF THE INVENTION

A further object of the invention is to introduce the mercury continuously and substantially steadily into the pores of the solid under examination, so that thermodynamic equilibrium is observed at all times.

We have developed a simple, reliable, inexpensive and easily operated method and apparatus which produces a curve which is a very precise image of the pressure increase in the sample holder as a function of time, with excellent repeatability.

In addition, the sample holders required for the method and apparatus of the invention are very inexpensive..

In general, the invention concerns a method of mercury intrusion into a porous sample comprising the following steps:

a) a step for determining the compressibility of the mercury and the various elements with variable volumes, also the elasticity of the materials, for an empty sample holder under suitable mercury injection rate programming conditions;

b) a determination step carried out in the presence of a sample, under identical conditions to those of the preceding step;

c) comparing the two curves obtained above.

Determination steps a) and b) consist in measuring the displacement of the pump syringe to a very high degree of accuracy, resulting in a measurement of the volume of mercury introduced into the pores of the solid as a function of time. This measurement is carried out at time intervals which can be as low as a fraction of a second. At the same time, the pressure increase is measured as a function of time using 1 or 2 sensors which cover pressure ranges of, for example, 1 to 100 bar, ie., $10^5$ Pascal to $10^7$ Pascal and 1 to 4500 bar, ie., $10^5$ Pascal to $4.5.10^2$ MPa. These measurements are also made at time intervals which can be as low as a fraction of a second, ie., practically continuously.

More precisely, the invention concerns a method for determining pore volume parameters of a solid sample by porosimetry, characterised in that the following steps are carried out:

a) an empty sample holder is filled with a non wetting liquid with a compressibility ratio which is less than or equal to that of mercury, such as mercury;

b) the sample holder is placed in a chamber in a high pressure cell, the chamber being in communication with the sample holder;

c) the high pressure cell chamber is filled with said liquid using a suitable pump means;

d) the filled chamber is isolated;

e) a substantially steady flow of said liquid is programmed and introduced into the cell chamber by the pump means for a set period of time, and the volume of liquid introduced is thereby continuously calculated;

f) the pressure corresponding to the volume of liquid introduced during said period is continuously measured;

g) the sample holder is emptied;

h) a known weight of a sample is introduced into the sample holder which is filled with said liquid;

i) the sample holder is placed in the high pressure cell chamber;

j) steps c), d) and e) are repeated in the presence of the sample in the sample holder;

k) the pressure corresponding to the volume of liquid introduced into the cell chamber containing the sample is continuously measured during said period; and l) suitable processing means continuously determine the volume of liquid introduced into the sample per unit weight for each pressure measurement obtained from steps f) and k) and the pore volume parameters per unit weight of the sample are thereby calculated.

Kelvin's law predicts that each pressure point corresponds to a pore radius.

The non wetting liquid with a compressibility ratio less than or equal to that of mercury is preferably mercury itself.

In accordance with one feature of the method, the steady flow of non wetting liquid into the high pressure cell chamber is programmed, both with and without the sample, to be at least $10^{-4}$ mm$^3$.s$^{-1}$, preferably between $1.5 \times 10^{-3}$ mm$^3$.s$^{-1}$ and 1 mm$^3$.s$^{-1}$. Syringe pumps are particularly adapted for regular and precise delivery of such flow rates.

Thermodynamic equilibrium is considered to be observed under these conditions.

In a further feature, these measurements are carried out at time intervals of less than 5 seconds, preferably less than one second, using pressure sensors. In this way, depending on the response time of the sensors, 2000 to 5000 measurements can be taken during a time period of about twenty minutes, for example.

It is also possible to calculate a histogram showing the pore size distribution in the sample from measurements of the pore volume of the sample, using appropriate processing means.

The invention further concerns an apparatus for determining the pore volume of a solid sample. In general, it comprises (FIG. 4) a substantially sealed high pressure cell (50) comprising a chamber (10a), a sample holder (1b) provided with a closure including a tube (21b) which is open at its two extremities and of suitable diameter, the sample holder being mounted in said chamber and communicating therewith via said tube, means (2) for creating a vacuum connected to said chamber, and means (8) for supplying a non wetting liquid such as mercury connected to the chamber. The apparatus is characterised in that it includes pump means (9) connected to the chamber and to the liquid supply means for delivering said liquid under pressure, means (40) connected to the pump for programming a steady supply rate over a set period of time, at least one pressure sensor (15) downstream of the pump means adapted to read the pressure continuously, and means (41) for signal collection and processing connected to the pressure sensor and to the means for programming the liquid supply, adapted to determine the pore volume parameters.

In one embodiment of the apparatus, the cell comprises two orifices (30, 14b), one of which (30) provides communication between the chamber and the pump means, and closure (14) including tube (14a) which is adapted either to bring the second orifice (14b) into communication with the chamber and an expansion chamber (13) for said liquid, or to close the second orifice.

In a further embodiment, the cell comprises a single orifice (30) which brings the chamber (10a) into communication either with the pump means (4), or with the vacuum creating means (2), by means of an appropriate valve between the pump means and the orifice.

BRIEF DESCRIPTION OF THE DRAWINGS

The invention will be better understood from FIG. 4 which schematically illustrates an apparatus for carrying out the method, and FIGS. 1 to 3 which respectively show a curve of pressure as a function of time in a cell without a sample, then with a sample, and finally a curve showing the volume of mercury introduced as a function of pore size.

DETAILED DESCRIPTION OF THE INVENTION

Figure 1:
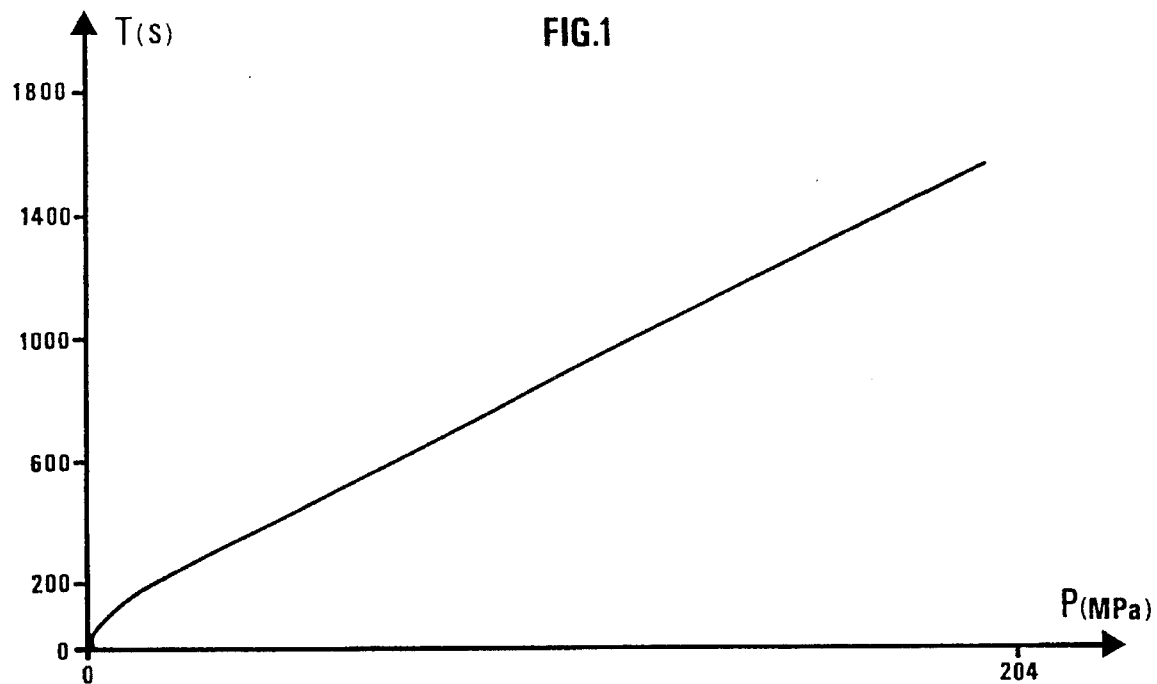

The apparatus comprises sample holder 1 positioned in a low pressure assembly connected to mercury reservoir (3) via line (20) on which valve V4 is mounted. The sample holder has a closure (1a) in its upper portion which comprises tube (21) which is open at both its extremities and is connected to line (20) by filling needle (22). In order to determine the pore volume parameters of powders, it is preferable that the annular space between the wall of the sample holder and tube (21) has a volume at least equal to that of the powder.

The upper portion of the tube is connected via line (23) equipped with valve V1 to vacuum pump (2), provided with vacuum gauge (4).

Vacuum pump (2) provided with vacuum gauge (4) creates a vacuum either in high pressure cell (50) via lines (26 and 27) containing valve V3, or in sample holder (1) via line (23) controlled by valve V1 and pressure sensor (5), or in the mercury reservoirs (3 and 8) via lines (26, 25) and valve V2 or lines (26, 27, 28) and valves V3, V8.

High pressure cell (50) comprises stainless steel cell body (10) which is adapted to resist very high pressures ($4.5 \times 10^2$ MPa) and contains chamber (10a) for sample holder (1b). Closure (11) closes the upper portion of cell body (10) by means of screw (12) and seals (not shown). The sample holder, which is held in chamber (10a) by suitable lugs, has closure (1d) in its upper portion provided with tube (21b) mentioned above. The upper portion of chamber (10a) into which tube (21b) opens is connected to transparent expansion chamber (13) via orifice (14b) and knurled closure (14) which has a tapered seal and which includes open ended tube (14a). This expansion chamber is connected via line (27) controlled by valve V3 to vacuum pump (2). The expansion chamber is also connected to mercury reservoir (8) via line (28) provided with valve V8.

In order to prevent oxidation of the mercury during depressurisation to atmospheric pressure, nitrogen is fed from reservoir (24) to reservoir (8) or expansion chamber (13) via lines (25a and 28) controlled by valves V8 and V7, to sample holder (1) via lines (25 and 25b) controlled by valve V6 or to reservoir (3) via line (25) provided with valve V5. Regulating valve (7) connected to nitrogen reservoir (24) controls the pressure in the various lines.

A further capillary (30) in the lower portion of chamber (10a) connects it via line (31) with high pressure syringe pump (9) (NOVA SWISS). The pump is filled with mercury from mercury reservoir (8) controlled by valves V9 and V10 and pressure sensors (15 and 16).

Safety valves are also positioned in the apparatus for protection purposes, but are not shown in the Figure.

Means (40) for programming the different parameters of the syringe pump ensure the required increase in pressure in or introduction of mercury into the measuring cell.

Finally, data collection and processing means (41) are adapted to collect and process the signals from the pressure sensors (15 and 16) and the mercury volume sensors, delivered as a function of time by means (40).

Each evaluation is preceded by placing the whole apparatus under vacuum to eliminate traces of air.

Porosity determination is carried out in two steps:

1) a reference measurement is made for a given sample holder in high pressure cell (50). This measurement is carried out once and the parameters are stored. It can be checked at regular intervals;

2) the porosity of a solid sample is evaluated.

1. Reference Measurement 1.1 Low Pressure

Sample holder (1) is completely empty. It is positioned in the low pressure assembly. A vacuum is created in sample holder (1) and in mercury reservoir (3) by means of vacuum pump (2). The vacuum level is less than 1 Pa and is read on vacuum gauge (4) and stored in the computer. Valves V1 and V2 enable the vacuum to be created in the low pressure assembly. When this operation is complete, valve V4 is opened, and with the additional use of valve V5, the reservoir is brought to a fixed pressure of between $1.10^5$ and $1.5.10^5$ Pa using nitrogen circuit (24, 25, V5) which is regulated by pressure regulator (7) coupled to pressure sensor (6). The mercury is then transferred from reservoir (3) to sample holder (1). The sample holder is filled with mercury, valve V4 is closed and the sample holder is brought to a fixed pressure of between $1.10^5$ and $1.5.10^5$ Pa using valve V5 and the regulated nitrogen circuit. 1.2 High Pressure A vacuum is created in high pressure (HP) cell (50) and syringe pump (9) connected to HP Cell (50) is at its origin, filled with mercury via valve V9 and mercury reservoir (8).

Approximately half the volume of chamber (10a) is filled with mercury from (8) via V9.

The mercury-filled sample holder described above is then positioned in chamber (10a) of cell (50). Closure (11) and screw (12) close the HP cell. A vacuum is reapplied to the high pressure assembly via V3 and syringe pump (9) is activated. The mercury fills chamber (10a) of the HP cell and overflows into transparent expansion chamber (13).

The vacuum is released and a nitrogen pressure of between $1.10^5$ and $1.5.10^5$ Pa is applied via (13). The syringe pump is stopped.

The HP cell is isolated from the low pressure circuits by knurled closure (14) with a tapered seal. The point of origin of the pressurising pump is registered, recorded and stored as well as the value given by the high pressure sensor(s) (15 and 16).

The pump rate is fixed, for example at 0.015 cm³ min⁻¹, and the increase in pressure is recorded in 4 to 5000 data points.

The reference measurement for a given sample holder is stored in the computer memory. This value has good reproducibility, ie., ±0.5%.

2. Determination of the Pore Volume of a Solid Sample

The pore volume of a sample is determined in a sample holder whose reference value has been evaluated.

The determination proceeds using the same protocol as that for the reference.

2.1 Low Pressure

A certain amount of pretreated solid sample is weighed into the sample holder. The sample holder is then filled with mercury following protocol 1.1.

Once this operation is complete, the sample holder, containing the sample for porosity evaluation and filled with mercury, is weighed.

The difference in weight between the same sample holder without and with the solid incidentally gives the volume occupied by a known weight of sample and thus gives the grain density of the solid under consideration.

2.2 High Pressure

The sample holder is then placed in the high pressure cell. The protocol is the same as that used during high pressure reference determination.

This provides two tables of values: pressures, volumes introduced or displaced, time. The point to point difference gives the volume of mercury introduced into the solid at a particular, substantially continuously increasing pressure. The number of data points (for example, 2000 to 5000 points) is limited by the response time of the sensor (10 ms, for example).

The apparatus of the invention is of greatest use in the study of the porous structure of materials by intrusion of a non wetting liquid, for example mercury, into pores in solids (see, for example "Adsorption, Surface Area and Porosity", S J GREGG and K S W SING, Academic Press Inc., 2nd Edition 1982).

The following Example illustrates the invention without in any way limiting its scope.

The pore volume of an alumina sample was determined by mercury intrusion into its pores, using an apparatus of the invention.

Pretreatment

Powdered, granular, particulate etc solid was pretreated in an oven at 250° C. for 12 hours to remove impurities contained therein (for example, water).

Reference Measurement for Sample Holder

The reference measurement for the sample holder was determined in accordance with the protocol described in 1.1 and 1.2, ie., a mercury flow rate of 0.015 mm³.s⁻¹ and a scan time of 0.5 second. A pressure of 200 MPa was reached. This produced a table of time, ie., the volume of mercury displaced by the syringe pump, as a function of pressure. The volume displaced included the compressibility of the mercury, the seals and expansion of the materials present. The reference measurement is shown as the curve in FIG. 1. The reproducibility was better than 0.5%.

Figure 2:
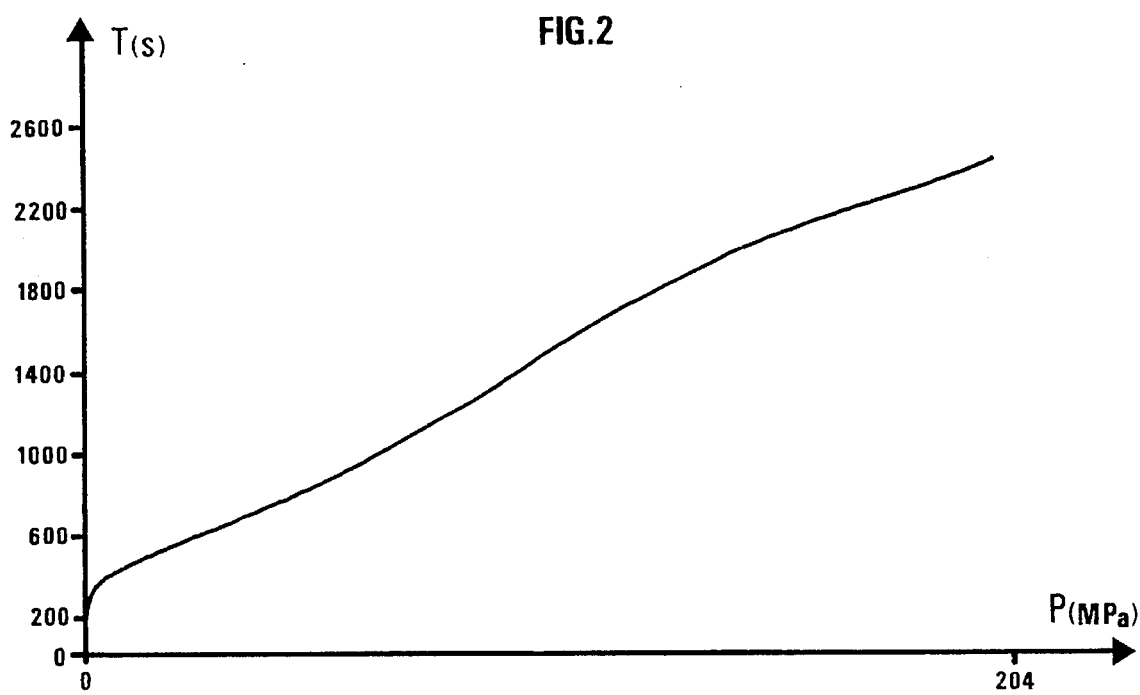

Determination 339 mg of an alumina sample, with a specific surface area of about 100 m²/g (RHONE-POULENC), was weighed into the cell for which the reference measurement had been carried out; the determination protocol described (2.1 and 2.2) was followed to produce a table of time and thus volume of mercury introduced into the pores, pressures and pore diameters by application of Kelvin's law (FIG. 2).

Figure 3:
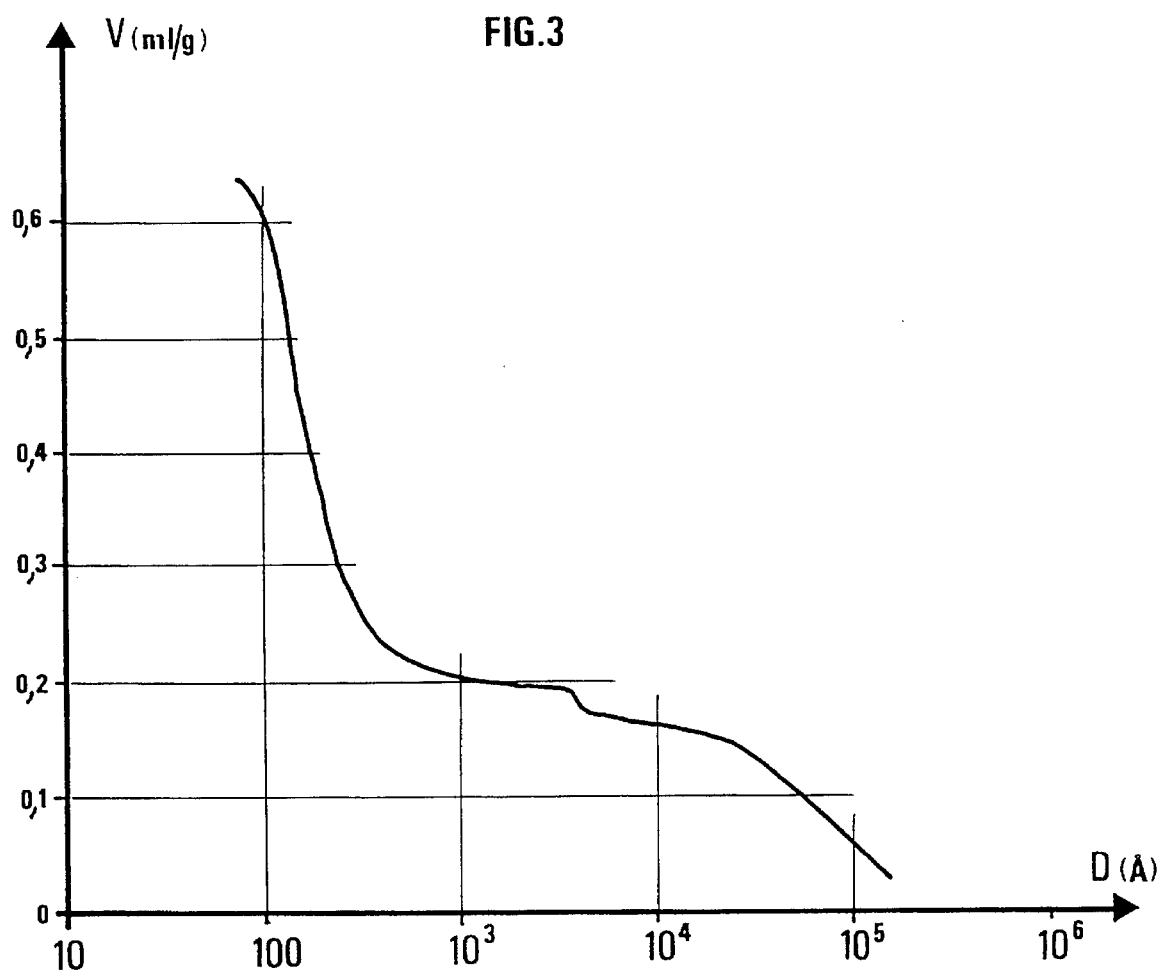
Figure 4:
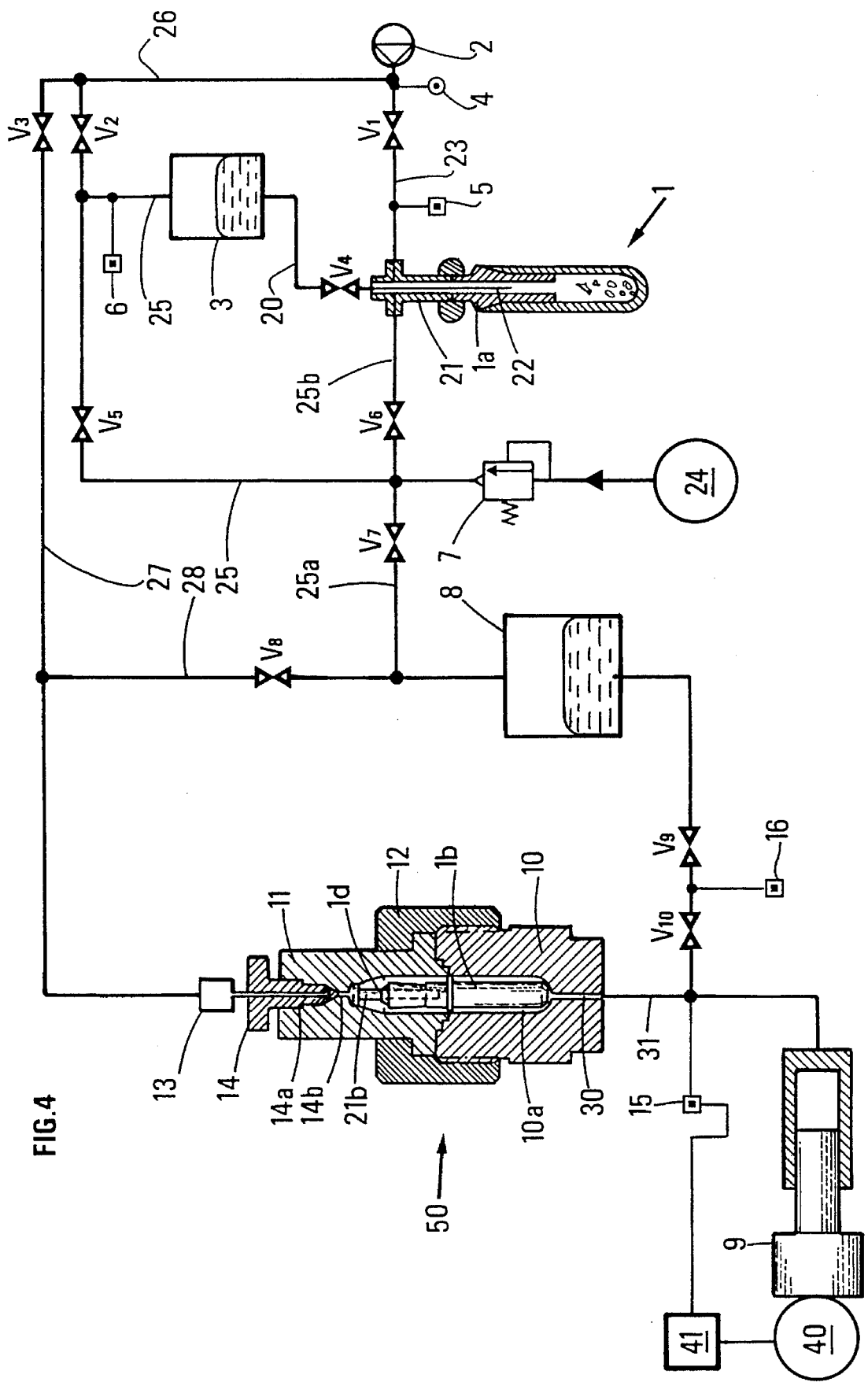

For each of these values of volume introduced as a function of pressure, the corresponding value for the reference was derived by calculation. This produced a new table of volume of mercury expressed in milliliters per gram of sample introduced into the pores of the solid as a function of the pressure and thus of the pore diameter (FIG. 3) expressed in angstroms (1 Å=$10^{-10}$ m).

The pressure in this Example was $2.10^2$ MPa.

It is clear that, during depressurisation to atmospheric pressure, the volume of mercury displaced from the sample towards the syringe pump can be measured as a function of the pressure drop and the volume of mercury retained in the pores can thus be calculated. This measurement helps in the formulation of hypotheses regarding the size or shape of the pores.

We claim:

1. Apparatus for determining the pore volume parameters of a solid sample comprising a substantially sealed high pressure cell (50) containing a chamber (10a), a sample holder (1b) provided with a closure including a tube (21b) which is open at its two extremities and of a suitable diameter, the sample holder being mounted in said chamber and communicating therewith via said tube, means (2) for creating a vacuum connected to said chamber, and means (8) for supplying a non wetting liquid such as mercury connected to the chamber, the apparatus being characterised in that it includes pump means (9) connected to the chamber and to the liquid supply means for delivering said liquid under pressure, means (40) connected to the pump for programming a steady supply rate over a set period of time, at least one pressure sensor (15) downstream of the pump means adapted to read the pressure continuously, and means (41) for signal collection and processing connected to the pressure sensor and to the means for programming the liquid supply, adapted to determine the pore volume parameters of the sample.

2. Apparatus according to claim 1 wherein the cell comprises
   (a) two orifices (30, 14b), one of which (30) provides communication between the chamber and the pump means, and the second orifice (14b) provides communication between the chamber and an expansion chamber (13),
   (b) and closure (14) including tube (14a) which is adapted to bring the second orifice (14b) into communication with the chamber and an expansion chamber (13) for said liquid, or to close the second orifice.

3. Apparatus according to claim 1 wherein the cell comprises a single orifice (30) which brings the chamber (10a) into communication either with a pump means (4), or with the vacuum creating means (2), by means of an appropriate valve between the pump means and the orifice.

4. Apparatus according to claim 1 wherein the sample holder comprises a closure (1d) including a small diameter tube (21b) which is open at both its extremities.

5. Apparatus according to claim 1 wherein the pump means is a syringe pump.

6. Use of an apparatus according to claim 1 to determine the pore volume of a catalyst, rock, cement or ceramic material.

7. Method for determining pore volume parameters of a solid sample by porosimetry, characterised in that the following steps are carried out:
   a) an empty sample holder is filled with a non wetting liquid with a compressibility ratio which is less than or equal to that of mercury, such as mercury;
   b) the sample holder is placed in a chamber in a high pressure cell, the chamber being in communication with the sample holder;
   c) the high pressure cell chamber is filled with said liquid using a suitable pump means;
   d) the filled chamber is isolated;
   e) a substantially steady flow of said liquid is programmed and introduced into the cell chamber by the pump means for a set period of time, and the volume of liquid introduced is thereby continuously calculated;
   f) the pressure corresponding to the volume of liquid introduced during said period is continuously measured;
   g) the sample holder is emptied;
   h) a known weight of a sample is introduced into the sample holder which is filled with said liquid;
   i) the sample holder is placed in the high pressure cell chamber;
   j) steps c), d) and e) are repeated in the presence of the sample in the sample holder;
   k) the pressure corresponding to the volume of liquid introduced into the cell chamber containing the sample is continuously measured during said period; and
   l) suitable processing means continuously determine the volume of liquid introduced into the sample per unit weight for each pressure measurement obtained from steps f) and k) and the pore volume parameters per unit weight of the sample are thereby calculated.

8. Method according to claim 7 wherein a steady flow of non wetting liquid into the high pressure cell chamber is programmed, both with and without the sample, to be at least $10^{-4}$ mm$^3$.s$^{-1}$, preferably between $1.5\times10^{-3}$ mm$^3$.s$^{-1}$ and 1 mm$^3$.s$^{-1}$.

9. Method according to claim 7 wherein the pressure is measured at time intervals of less than 5 seconds, preferably less than 1 second.

10. Method according to claim 7 wherein the non wetting liquid is mercury.

11. Method according to claim 7 wherein the pump means is a syringe pump.

* * * * *